(12) United States Patent
Curran et al.

(10) Patent No.: US 7,713,508 B2
(45) Date of Patent: May 11, 2010

(54) THIATION OF CARBON NANOTUBES AND COMPOSITE FORMATION

(75) Inventors: Seamus A. Curran, Las Cruces, NM (US); Amanda V. Ellis, Kohimarama (NZ)

(73) Assignee: Arrowhead Center, Inc., Las Cruces, NM (US)

( * ) Notice: Subject to any disclaimer, the term of this patent is extended or adjusted under 35 U.S.C. 154(b) by 1153 days.

(21) Appl. No.: 11/086,116

(22) Filed: Mar. 21, 2005

(65) Prior Publication Data

US 2006/0079626 A1 Apr. 13, 2006

Related U.S. Application Data

(60) Provisional application No. 60/634,163, filed on Dec. 7, 2004, provisional application No. 60/554,593, filed on Mar. 19, 2004, provisional application No. 60/554,594, filed on Mar. 19, 2004.

(51) Int. Cl.
*D01F 9/12* (2006.01)
*B82B 3/00* (2006.01)

(52) U.S. Cl. .................................. 423/447.1; 977/847

(58) Field of Classification Search .............. 423/447.1, 423/460; 977/847
See application file for complete search history.

(56) References Cited

U.S. PATENT DOCUMENTS

| | | | |
|---|---|---|---|
| 5,232,630 A | 8/1993 | Pouwer | |
| 6,331,262 B1 | 12/2001 | Haddon et al. | |
| 6,368,569 B1 | 4/2002 | Haddon et al. | |
| 6,426,134 B1 | 7/2002 | Lavin et al. | |
| 6,495,680 B1 | 12/2002 | Gong | |
| 6,645,455 B2 | 11/2003 | Margrave et al. | |
| 6,768,246 B2 | 7/2004 | Pelrine et al. | |
| 6,790,425 B1 | 9/2004 | Smalley et al. | |
| 2002/0019554 A1 | 2/2002 | Benicewicz et al. | |
| 2002/0172963 A1 | 11/2002 | Kelley et al. | |
| 2003/0012723 A1 | 1/2003 | Clarke | |
| 2003/0012951 A1 | 1/2003 | Clarke et al. | |
| 2003/0124572 A1 | 7/2003 | Umek et al. | |
| 2003/0133865 A1 | 7/2003 | Smalley et al. | |
| 2003/0135971 A1 | 7/2003 | Liberman et al. | |
| 2003/0170167 A1 | 9/2003 | Nikolaev et al. | |
| 2003/0180526 A1 | 9/2003 | Winey et al. | |
| 2003/0185741 A1 | 10/2003 | Matyjaszewski et al. | |
| 2003/0220424 A1 | 11/2003 | Schofalvi et al. | |
| 2004/0028901 A1 | 2/2004 | Rumpf et al. | |
| 2004/0086423 A1 | 5/2004 | Wohlstadter et al. | |
| 2004/0126303 A1 | 7/2004 | Hwang | |

OTHER PUBLICATIONS

Azamian, Bobak R., et al., "Directly observed covalent coupling of quantum dots to single-wall carbon nanotubes", *Chem. Commun.*, The Royal Society of Chemistry,(Feb. 5, 2002),366-367.

Byfield, M. P., et al., "Biochemical aspects of biosensors", *Biosensors & Bioelectronics*, vol. 9, Elsevier Science Publishers Ltd.,(1994),373-400.

Chakrapani, Nirupama, et al., "Spectral fingerprinting of structural defects in plasma-treated carbon nanotubes", *J. Mater. Res.*, vol. 18, No. 10, Materials Research Society,(Oct. 2003),2515-2521.

Curran, Seamus A., et al., "A Composite from Poly(m-phenylenevinylene-co-2,5-dioctoxy-p-phenylenevinylene) and Carbon Nanotubes: A Novel Material for Molecular Optoelectronics", *Adv. Mater.*, vol. 10, No. 14, (1998),1091-1093.

Curran, S. A., et al., "Functionalization of carbon nanotubes using phenosafranin", *Journal of Chemical Physics*, vol. 120, No. 10, American Institute of Physics,(Mar. 8, 2004),4886-4889.

Dong, Jian, et al., "Raman difference spectroscopic studies of dithiobenzoyl substrate and product analogs binding to the enzyme dehalogenase: pi-electron polarization is prevented by the C=) to C=S substitution", *Journal of Raman Spectroscopy*, vol. 31, John Wiley & Sons, Ltd.,(2000),365-371.

Dresselhaus, M. S., et al., "Raman spectroscopy on isolated singl wall carbon nanotubes", *Carbon*, vol. 40, Elsevier Science Ltd.,(2002),2043-2061.

Ellis, A. V., et al., "Hydrophobic Anchoring of Monolayer-Protected Gold Nanoclusters to Carbon Nanotubmes", *Nano Letters*, vol. 3, No. 3, American Chemical Society,(2003),279-282.

Ferrari, Andrea C., "Determination of bonding in diamond-like carbon by Raman spectroscopy", *Diamond and Related Materials*, vol. 11, Elsevier Science B.V.,(2002),1053-1061.

Holzinger, Michael, et al., "Sidewall Functionalization of Carbon Nanotubes", *Angew. Chem. Int. Ed.*, vol. 40, No. 21,(2001),4002-4005.

Hu, H., et al., "Determination of the acidic sites of purified single-walled carbon nanotubes by acid-base titration", *Chemical Physics Letters*, vol. 345, Elsevier Science B.V.,(Sep. 7, 2001),25-28.

Kameyama, Atsushi, et al., "Novel Sequence-Ordered Polymers by Transforation of Polymer Backbone: Quantitative and Regioselective Insertion of Thiiranes into Poly(S-aryl Thioester)", *Macromolecules*, vol. 32, American Chemical Society,(1999),1407-1412.

Kastner, J., et al., "Resonance Raman and infrared spectroscopy of carbon nanotubes", *Chemical Physics Letters*, vol. 221, Elsevier Science B.V.,(Apr. 15, 1994),53-58.

Kudelski, Andrzej, "Structures of monolayers formed from different HS—(CH2)2—X thiols on gold, silver and copper: comparitive studies by surface-enhanced Raman scattering", *Journal of Raman Spectroscopy*, vol. 34, John Wiley & Sons, Ltd.,(2003),853-862.

Li, Yan-Hui, et al., "Self-organized Ribbons of Aligned Carbon Nanotubes", *Chem. Mater.*, vol. 14, American Chemical Society,(2002),483-485.

(Continued)

*Primary Examiner*—Stuart Hendrickson
(74) *Attorney, Agent, or Firm*—Vidal A. Oaxaca; Deborah A. Peacock; Samantha A. Updegraff (57) ABSTRACT

The present invention comprises nanotube structures comprising nanotubes covalently bonded via chemically reactive groups on the outer walls of the nanotubes and methods for forming the covalently bonded nanotube structures. The present invention also comprises materials comprising the functionalized nanotubes covalently bonded to organic based monomers and/or polymers, and methods for their formation.

16 Claims, 7 Drawing Sheets

OTHER PUBLICATIONS

Lim, Jong K., et al., "Selective thiolation of signle-walled carbon nanotubes", *Synthetic Metals*, vol. 139, Elsevier B.V.,(2003),521-527.

Liu, Jie , et al., "Fullerene Pipes", *Science*, vol. 280,(May 22, 1998),1253-1256.

Lordi, Vincenzo , et al., "Method for Supporting Platinum on Single-Walled Carbon Nanotubes for a Selective Hydrogenation Catalyst", *Chem. Mater.*, vol. 13, American Chemical Society,(2001),733-737.

Nemanich, R. J., et al., "First- and second-order Raman scattering from finite-size crystals of graphite", *Physical Review B*, vol. 20, No. 2, The American Physical Society,(Jul. 15, 1979),392-401.

Porter, Lon A., et al., "Gold and Silver Nanoparticles Functionalized by the Adsorption of Dialkyl Disulfides", *Langmuir*, vol. 14, American Chemical Society,(1998),7378-7386.

Sudalai, Arumugam , et al., "Phosphorus Pentasulfide: A Mild and Versatile Catalyst/Reagent for the Preparation of Dithiocarboxylic Esters", *Organic Letters*, vol. 2, No. 20, American Chemical Society,(2000),3213-3216.

THIATION OF CARBON NANOTUBES AND COMPOSITE FORMATION

CROSS-REFERENCE TO RELATED APPLICATIONS

This application claims the benefit of the filing of: U.S. Provisional Patent Application Ser. No. 60/554,594, entitled "Covalent Bonding of Individual Nanotubes and Nanowires", filed Mar. 19, 2004; U.S. Provisional Patent Application Ser. No. 60/554,593, entitled "Composite Formation Through Covalent Bonding Using Nanotubes and Polymers", filed Mar. 19, 2004; and U.S. Provisional Patent Application Ser. No. 60/634,163, entitled "Thiation of Carbon Nanotubes Using Phosphorus Pentasulfide", filed Dec. 7, 2004, and the specifications of those applications are incorporated herein by reference.

BACKGROUND OF THE INVENTION

1. Field of the Invention (Technical Field)

The present invention relates to the use of bridging molecule complexes to covalently bond nanotubes and to use nanotubes for the formation of composite materials comprising functionalized nanotubes and organic based monomers and/or polymers.

2. Background Art

Carbon nanotubes are inert but can be chemically functionalized. Functionalization and derivatization increases interfacial binding in composites thus providing a mechanism for connecting nanotubes together and/or to substrates. Because of the limited scope of direct covalent sidewall functionalization at defect sites, traditional chemical treatments such as wet oxidation in concentrated $HNO_3/H_2SO_4$ are used to functionalize nanotube surfaces with hydroxyl (—OH), carboxyl (—COOH) and carbonyl (>C=O) groups. In the art, carboxylic groups have been converted to acid chloride using thionyl chloride with subsequent amide linkage of an aminoalkanethiol to single-walled nanotubes ("SWNT's"). More recently SWNT's have been derivatized by thionyl chloride to produce thiols on the ends of SWNT's.

Polymer/nanotube nanocomposites are of interest because of their potential structural and electronic applications. However, the chemical interaction between polymers and nanotubes is typically limited to van der Waals forces and weak electrostatic interactions. It is known in the art that functionalization enhances the interaction between nanotubes and other organic matrices.

The fundamental control over composite morphologies and interfacial chemical interactions is critical for dramatically enhancing their performances in electronic applications. Although covalent attachment of polymers to nanotubes has been achieved, high loadings with poor nanotube dispersions dominate composite formation and device fabrication. Ion-conducting polymers, or polymers containing conductive fillers such as carbon black (5-30% by weight loading), are typically employed for electronic applications. However, they suffer from several drawbacks including having high dopant or filler loadings, being brittle, and being opaque as thin films. Carbon nanotubes offer a viable alternative. However, although single-walled carbon nanotubes (SWCNT's) provide the highest conductivities at low loadings, homogeneous dispersion is still problematic. In the prior art, multi-walled carbon nanotube ("MWCNT") composites have offered a similar electronic potential to SWCNT's, but the loadings have been considerably higher, and the conductivities obtained have been considerably lower. Nanotubes in polymer composites do not have higher conductivities because of aggregation and tube-to-tube proximity. The result is that charge transport is via a hopping process where the charge carrier motion is determined by scattering from one conductive site to the next. Therefore, poor nanotube dispersion aggravates the poor and reduced carrier transport capability of the composite.

BRIEF SUMMARY OF THE INVENTION

The present invention comprises a nanotube structure comprising at least two covalently bonded nanotubes. The structure preferably comprises a dithioester. The dithioester comprises a reactive group of the formula S=C—$Ch_2$—S covalently bonded to the nanotubes. The dithioester preferably comprises a thiocarboxylic O-ester. The nanotubes preferably comprise multi-walled carbon nanotubes. In a preferred embodiment, the nanotubes are covalently bonded to at least one polymer or monomer.

The present invention also comprises a method of functionalizing at least one carbon nanotube comprising thiolating at least one surface of the at least one nanotube. Preferably, the least one nanotube is reacted with phosphorus pentasulfide to thiolate the at least one nanotube. The method preferably further comprises carboxylizing the at least one nanotube prior to reacting the at least one nanotube with phosphorus pentasulfide in solution to prepare a dithiocarboxylic ester of the formula wherein MWCNT is a multi-walled carbon nanotube.

The at least one carbon nanotube is preferably reacted with the phosphorus pentasulfide in a solution comprising anhydrous toluene. The solution is preferably refluxed, more preferably for between approximately 10 and 50 hours at from between approximately 0 and 150° C.

The method further comprises preferably covalently bonding a first of the at least one nanotube to a second of the at least one nanotube and polymerizing the nanotubes. The covalently bonded nanotubes preferably comprise nanotube dithioesters utilized as chain transfer agents for living free-radical polymerization of polymer monomers, preferably Reversible Addition-Fragmentation Chain Transfer Polymerization.

In one embodiment of the method, the nanotube dithioesters are preferably sonicated and reacted with a polymer. The nanotube dithioesters are preferably sonicated in a solution comprising anhydrous toluene. The polymer preferably comprises styrene.

Preferably, the reaction mixture comprising the nanotube dithioesters and the polymer is heated. The reaction mixture is then preferably cooled and tetrahydrofuran is preferably added to the reaction mixture. The reaction mixture is preferably added to methanol and a polymerized nanocomposite material is preferably precipitated.

Objects, advantages and novel features, and further scope of applicability of the present invention are set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

The present invention comprises nanotube structures comprising nanotubes covalently bonded via chemically reactive groups on the outer walls of the nanotubes and methods for forming the covalently bonded nanotube structures. The present invention also comprises materials comprising the functionalized nanotubes covalently bonded to organic based monomers and/or polymers, and methods for their formation.

By using a bridging molecule complex to bind nanotubes together covalently, the binding molecules can be polymerized. Functionalization and derivatization of nanotubes provides an increased interfacial binding in composites and provides a mechanism for connecting nanotubes together and/or to substrates. The invention is particularly useful in the aerospace and automotive fields and in the fields concerned with structural materials, packaging, and smart skins.

As used herein, the term nanotubes encompasses any carbon, nano-sized tubular structure referred to in the art as, but not limited to, nanotubes, nanofibrils, nanowires, single-walled nanotubes ("SWNT's"), multiple-walled nanotubes ("MWNT's"), multiple-walled carbon nanotubes ("MWCNT's"), double-walled carbon nanotubes, graphitic nanotubes, graphitic fibrils, carbon tubules, and buckeytubes. Boron and nitrogen doped nanotubes may also be utilized. In a preferred embodiment, MWCNT's are utilized and discussed in detail herein as they are illustrative of the present invention. However, the invention is applicable to other nanotubes.

The preferred embodiment of the present invention comprises directing the selective thiation of acid treated oxidized carbon nanotubes to dithioesters (thiocarboxylic O-esters) using a mild versatile catalyst including, but not limited to, phosphorus pentasulfide ($P_4S_{10}$) or Lawesson's reagent (2,4, Bis[4-methoxyphenyl]-1,3-dithia-2,4-diphosphetane-2,4-disulfide)($C_{14}H_{14}O_2P_2S_4$). Phosphorus pentasulfide is preferred because it provides an electrophilic single-step pathway for preparation of thiocarboxylic esters and thioesters when —COOH groups are reacted with thiols or alcohols in varying mole ratios.

The nanotubes may be obtained or prepared by any method known in the art. In a preferred embodiment, purified MWCNT's are synthesized by the arc-discharge method as known in the art, then sonicated while in suspension in an acid, preferably, but not limited to, $H_2SO_4/HNO_3$, to form carboxylic acid (—COOH) and hydroxyl (—OH) functional groups on the nanotube surface. The resulting suspension is filtered under vacuum, then the carboxylated MWCNT's are washed with de-ionized water.

Figure 1:
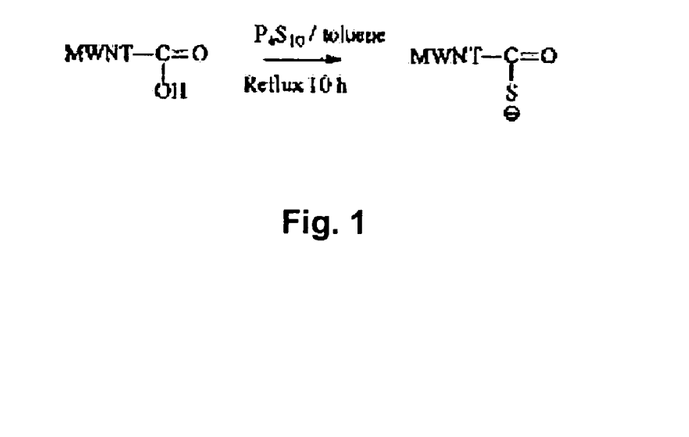
FIG. 1 shows a schematic illustration of the preferred embodiment of the present invention for the formation of thiolated multi-walled carbon nanotube ("MWCNT") surfaces.

FIG. 1 is a schematic illustrating the preferred embodiment of the synthesis of thiolated multi-walled nanotube surfaces. Preferably, their synthesis is achieved by combining dried, carboxylated MWCNT's and phosphorus pentasulfide in a solvent. Suitable solvents known in the art may be utilized. Preferably, the nanotubes and pentasulfide are combined in dried toluene. The solution is then refluxed, and the reaction can proceed under a wide range of temperatures, preferably from between approximately 0 and 150° C., more preferably from between approximately 80 and 140° C., and most preferably at approximately 140° C. The reaction time may vary from between approximately 10 to 50 hours, more preferably from between approximately 24 and 48 hours, and most preferably for approximately 48 hours. Following reaction, the reaction mixture is cooled and filtered under vacuum. The product is washed thoroughly, preferably with dried toluene. The thiolated nanotubes may be stored in a desiccator under nitrogen.

Figure 2:
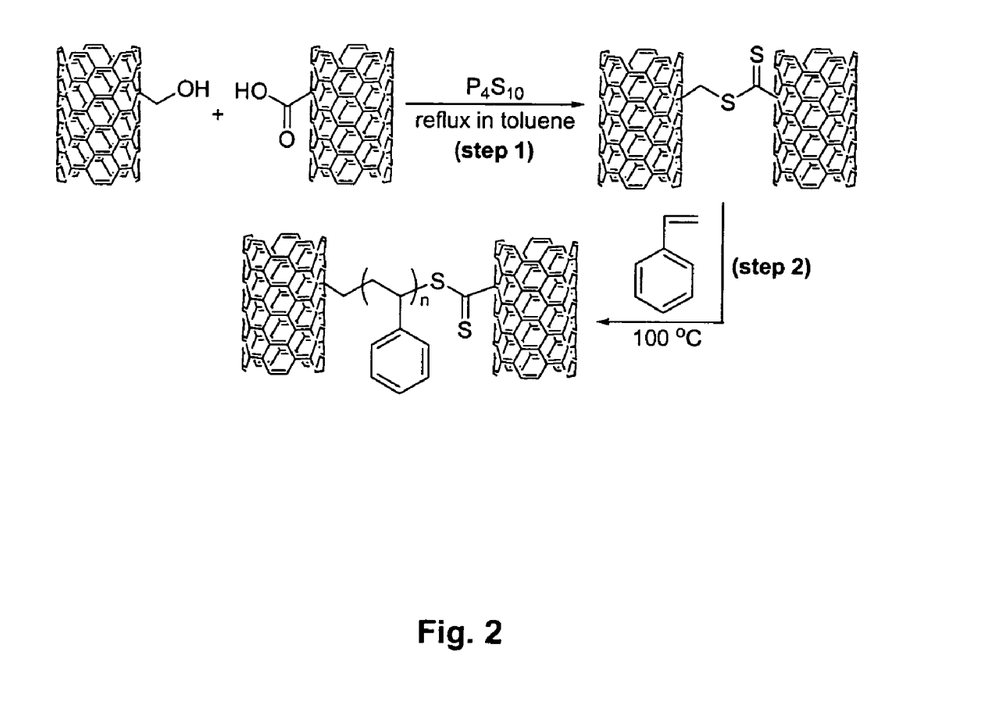
FIG. 2 shows a schematic illustration of the mechanism of the preferred embodiment of the present invention for the formation of thiocarboxylic O-ester and the covalent bonding of nanotubes to form composite materials.

Without being bound to a particular theory, the role of phosphorus pentasulfide is believed to be the activation of carboxylic functional groups for nucleophilic attack and thiolation of hydroxyl and carbonyl functional groups as shown in FIG. 2.

In another embodiment, the solution of MWNT's, phosphorus pentasulfide, and dried toluene is refluxed at approximately 115° C. for approximately 10 hours. If such relatively mild conditions are used, the occurrence of steric hindrance upon an initial thiocarboxyilic S-ester formation (containing the group O=C—$CH_2$—S) of the MWNT's may result in the absence of dithioesters. Consequently, the nanotube-thiocarboxylic S-esters are then preferably activated with phosphorus pentasulfide or with Lawesson's reagent, preferably phosphorus pentasulfide, in toluene, so that the C=O ester group is converted to C=S to yield nanotube-thiocarboxylic O-ester (dithioester) structures (S=C—$Ch_2$—S).

The MWCNT's are thus functionalized and covalently linked via intercalated dithiocarboxylic ester functional groups to form an oriented and bundled structure. The MWCNT's are linked together in either a side-on or end-on manner.

Figure 3:
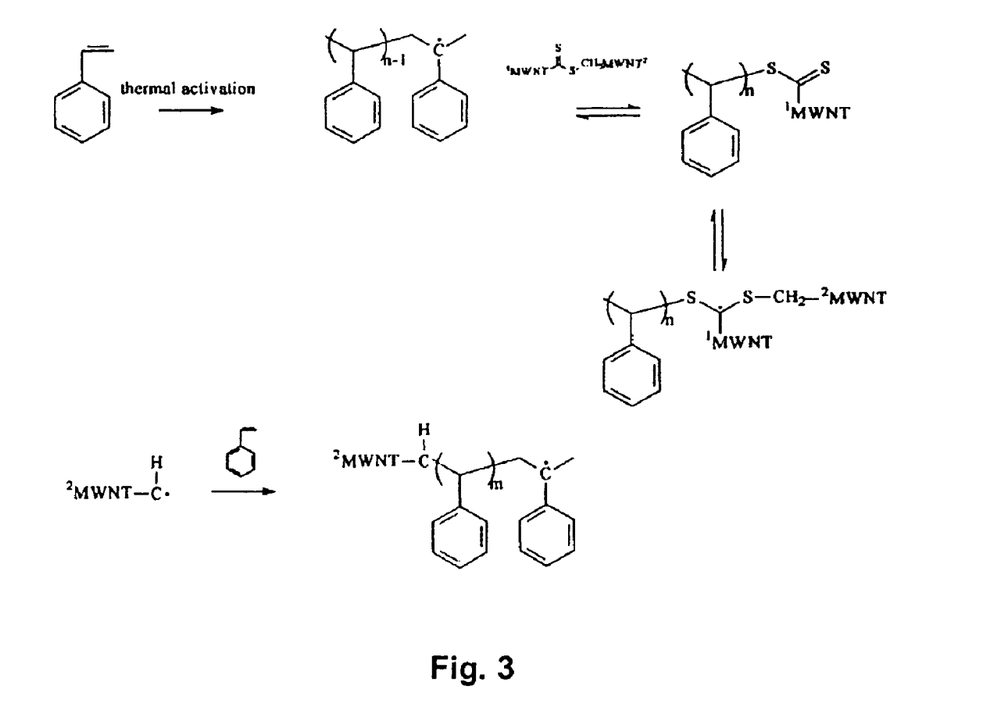
FIG. 3 shows a schematic illustration of nanotube/composite polymerization.

In a preferred embodiment of the present invention, as shown in FIG. 3, the resulting dithioesters are used as chain transfer agents ("CTA's") for living free-radical polymerization of polymer monomers in Reversible Addition-Fragmentation chain Transfer (RAFT) polymerizations for making strong composites from carbon nanotubes. This can be done using, for example, but not limited to, olefins, vinyl, methyl methacrylate (MMA), styrene, acrylamide (and their derivatives thereof), ethylene-vinyl alcohol, ethylene glycol, n-butyl acrylate, 2- and 4-vinylpyridine, acrylonitrile (and their derivatives thereof), and 2-metharyloxyethyl glucoside. The CTA enables control over polymer architecture (e.g., to create a block copolymer) and the molecular weight distribution (e.g., making all the chains of a very similar length).

In a preferred embodiment, depicted in FIG. 2, the functionalized, covalently bonded MWCNT's are covalently linked with polystyrene to form a well-dispersed nanocomposite with good conductivity through a simple RAFT method. The method, herein named "gRAFT" polymerization, comprises polymerizing styrene from the surface of dithiocarboxylic ester-functionalized MWCNT's to fabricate a unique composite material.

The preferred method for the formation of nanocomposites comprises sonicating dithioester MWCNT's in a solvent, preferably anhydrous toluene, and adding styrene. The mixture is preferably heated, preferably in a silicon oil bath, preferably at approximately 100° C. for approximately 24 hours with continuous stirring. The reaction mixture is preferably cooled, tetrahydrofuran ("THF") is preferably added, and the solution is preferably added to methanol. The resulting precipitate is preferably filtered and volatile materials removed under vacuum to yield the composite material.

The material comprises a smooth nanocomposite with enhanced electrical conductivity up to 33 $s \cdot m^{-1}$ with 0.90 wt % nanotube loadings and with improved thermal stability as compared with non-covalently linked MWCNT-polystyrene blends. The present invention thus provides a practical method for creating transparent antistatic coatings, electromagnetic insulating ("EMI") shields, and reinforced polymeric membranes in fuel cells.

EXAMPLES

1. Synthesis of Nanotube-dithioester Structures

Purified MWCNT's (100 mg), synthesized by the arc-discharge method, were sonicated (12 h, 130 W) in concentrated $H_2SO_4$:$HNO_3$ (7:3 vol/vol, 10 mL) to form carboxylic acid (—COOH) and hydroxyl (—OH) functional groups on the tube surface. The suspension was filtered under vacuum through a nylon Whatman microfilter (0.2 μm) and washed thoroughly with deionized water.

To form the dithiocarboxylic ester linkage, synthesis of thiolated MWCNT's was achieved by adding dried carboxylated MWCNT's (100 mg) to anhydrous toluene (50 mL) and phosphorus pentasulfide (10 mg, Aldrich) in a round bottomed flask (100 mL). The solution was refluxed (140° C., 48 h). The reaction mixture was cooled and filtered under vacuum through a nylon Whatman microfilter (0.2 μm), then the product was washed thoroughly with anhydrous toluene.

Dithiocarboxylic ester formation catalyzed by phosphorus pentasulfide was well documented for various alcohols and carboxylic acid. The role of phosphorus pentasulfide was proposed to be activation of carboxylic functional group for nucleophilic attack and thiolation of hydroxyl and carbonyl functional groups. The thiolated nanotubes were then stored in a desiccator under nitrogen.

2. Synthesis of Nanotube-polystyrene Nanocomposites

Nanocomposites were formed in a Schlenk flask with stirrer bar. Dithioester MWCNT's (91 164 mg) were sonicated (10 s, 130 W) in anhydrous toluene (1.00 mL, HPLC grade). Styrene (Baker, after removal of inhibitor) (2.00 mL, 1.82 g, 17.5 mmol) was added and the flask was sealed. The mixture was heated at 100° C. in a silicon oil bath for 24 h with continual stirring. To form the solid composite, the reaction mixture was cooled, THF (10 mL) added, and the solution was added to methanol (40 mL, HPLC grade). The precipitate was filtered and volatile materials were removed under vacuum to yield 1.68 g (92%) of light grey powder.

3. Results of Nanotube-dithioester Synthesis

Figure 4:
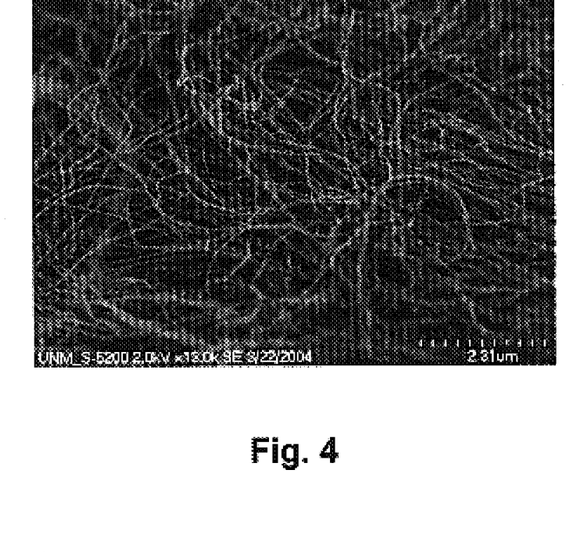
FIG. 4 shows a scanning electron micrograph of pristine MWCNT's.
Figure 5:
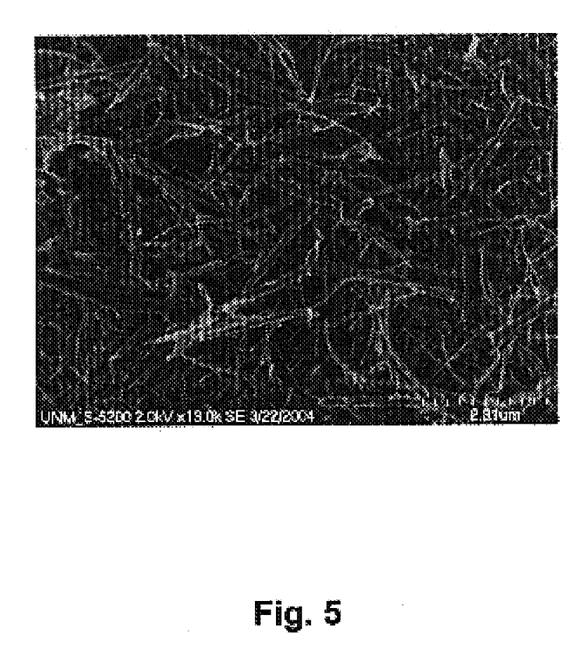
FIG. 5 shows a scanning electron micrograph of functionalized MWCNT's.

The functionalized MWCNT's were characterized by Raman Spectroscopy. As shown in FIG. 4, field emission scanning electron microscopy ("FESEM") show that, initially, the pristine MWCNT's were discrete nanotubes (~20-25-nm in diameter) held together in bundles via van der Waals forces. The nanotubes were of good quality and free of impurities (amorphous carbon). After functionalization with phosphorus pentasulfide resulting in dithiocarboxylic ester linkages, the nanotubes were no longer discrete but fused together into bundles either along the length of the body of the outer wall of the nanotubes or cross-linked from bundle to bundle, as shown in FIG. 5. The tubes were somewhat shortened due to the acid pre-treatment. However there was no evidence of exfoliation and the presence of any amorphous carbon particles from this treatment.

Figure 6:
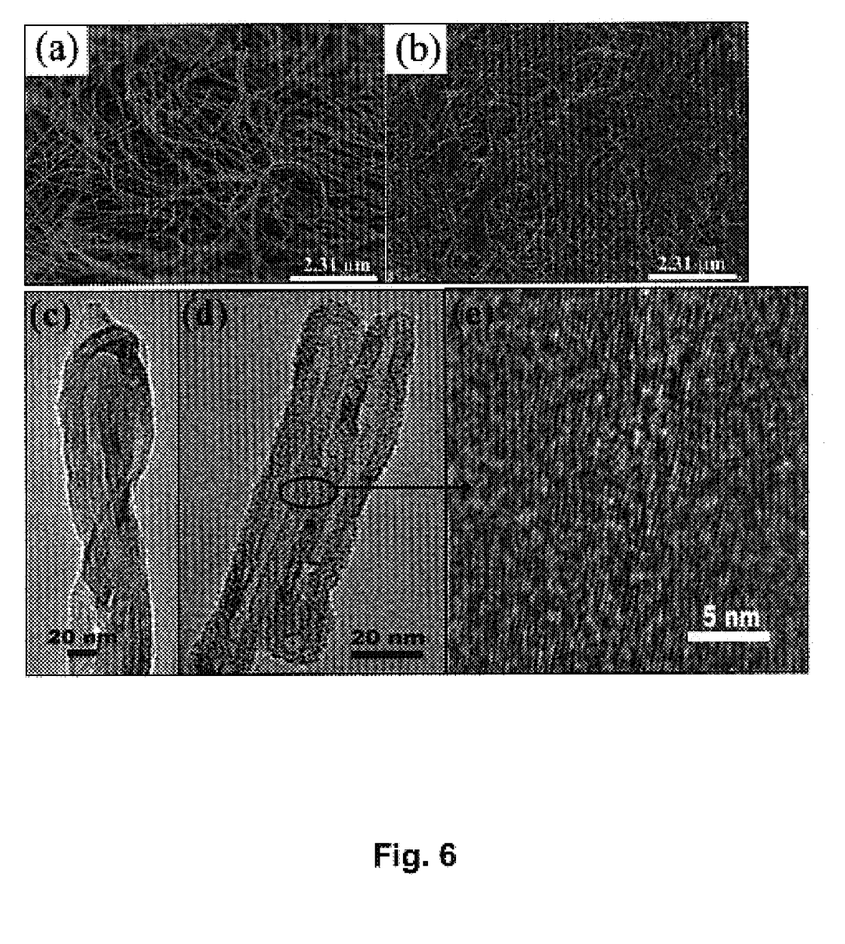
FIG. 6 shows (a) a scanning electron micrograph of purified, pristine MWCNT's, (b) a scanning electron micrograph of MWCNT's after a 12 hour acid treatment and thiation with phosphorus pentasulfide, (c) and (d) transmission electron micrographs of functionalized MWCNT's, and (e) the interface regions between a pair of covalently linked MWCNT's.

FIG. 6 shows FESEM images of the purified pristine MWCNT's prepared via the arc-discharge method (a) and MWCNT's after 12 hours of acid treatment and thiolation with phosphorus pentasulfide (b). Also shown are high resolution transmission electron microscopy ("HRTEM") images for the functionalized MWCNT's (~20 nm in diameter) (c) and (d) and the expanded region of interface between a pair of covalently linked MWCNT's showing uninterrupted lattice fringes of the outer graphitic walls of the tubes (e). For the HRTEM evaluation, the functionalized MWCNT's were dispersed in toluene and drop cast onto a Cu-grid with a holey carbon support prior to high-resolution transmission electron microscopy. The HRTEM micrographs (FIG. 6(c)) illustrate that the reaction products are bundles of aligned and closely bound (fused and tethered) nanotubes. The bundle represented is a group of three tubes overlapped by a fourth tube. FIG. 6(d), illustrates aligned attachment of the ends of two multi-walled nanotubes (~20 nm in diameter). Attachment at the ends predominates as acid attack results in a higher concentration of functional groups. FIG. 6(e), shows evidence of covalent attachment in which there is a continuation in the graphitic lattice fringes of one nanotube to the next—this is not observed for typical CNT bundles held together via van der Waals forces.

Figure 7:
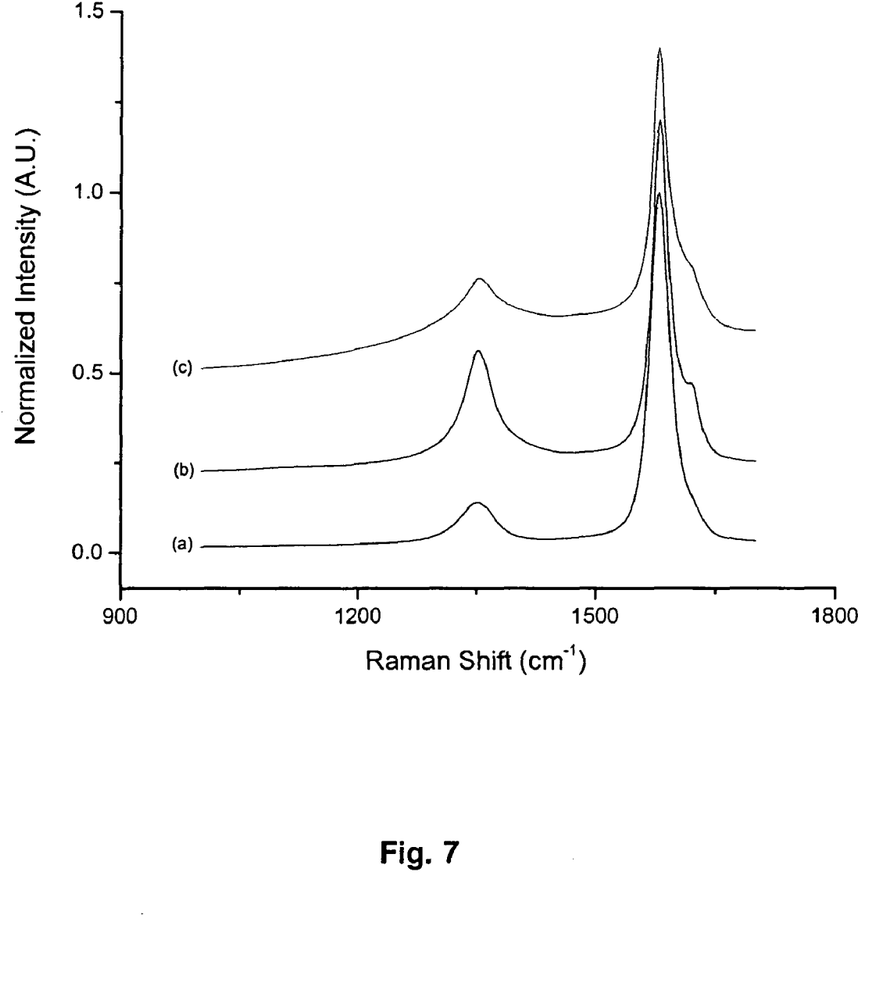
FIG. 7 shows Raman spectra of (a) pristine nanotubes, (b) acid treated nanotubes, and (c) thiolated nanotubes obtained using a Renshaw InVia Raman spectrometer equipped with a Raman Leica REO2 microscope.
Figure 8:
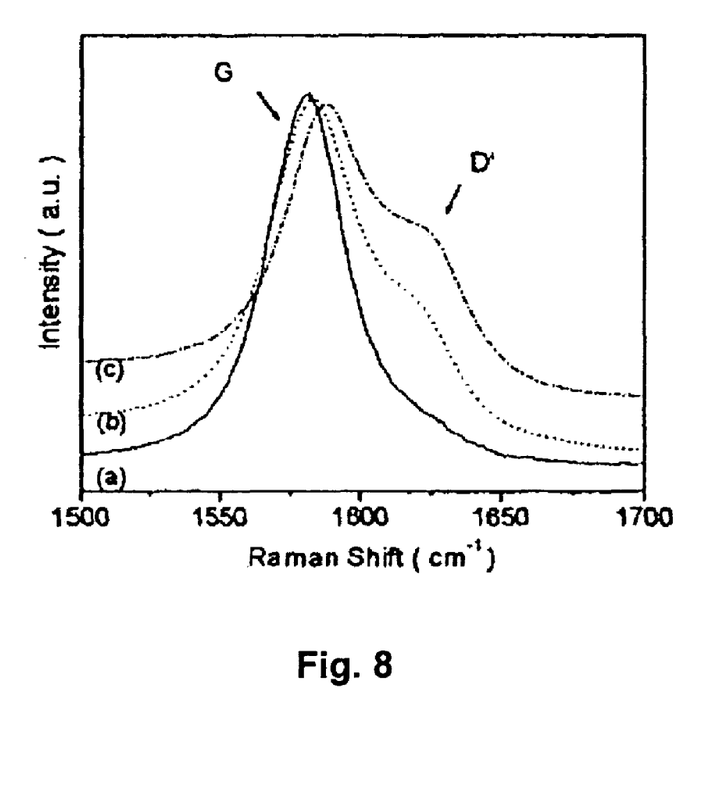
FIG. 8 shows a Raman spectrum as in FIG. 7.

Following thiolation, dramatic changes were observed in the Raman spectra as shown in FIG. 7 for the pristine MWCNT's (a), the acid treated MWCNT's (b), and the thiolated MWCNT's (c). All vibrations were significantly broadened, and the thiolated MWCNT's showed strong fluorescence from the bundling of the tubes through the newly formed covalent dithioester linkage. The D-mode at 1350 $cm^{-1}$ remained strong as a substantial lattice defect disorder was introduced, but its width was dramatically increased suggesting a greater dispersion of nanotube sizes resulting from the tubes being randomly linked to form such larger structures as seen in the SEM (FIG. 5). The G-band at 1580 cm$^{-1}$ remained unchanged and was shifted only slightly higher to 1582 cm$^{-1}$, again showing little or no formation of amorphous carbon. In addition, the D' peak changes at 1617 cm$^{-1}$ were expected because of, first, heavy acid treatent of the nanotubes, and then dampened when the linked species was formed. Most notable, as shown in FIG. 8, was the appearance of a new peak centred at 495 cm$^{-1}$, which is a combination of three vibrations v=475 cm$^{-1}$, 495 cm$^{-1}$, and 503 cm$^{-1}$ representing the different S═C─S stretching and bending modes in the dithioester linkage.

4. Results of Nanotube-styrene Nanocomposites

The resulting composite was characterized by Raman Spectroscopy. The thermal stability of the polymer matrix in the covalently linked MWCNT-polystyrene composite was significantly enhanced, as demonstrated by a 15° C. increase of the decomposition temperature than that of the non-covalently linked MWCNT-polystyrene blend. Thin films made from the composite with low MWCNT loadings (<0.9 wt %) were optically transparent and there was no evidence of aggregation of nanotubes in thin film or solution. The result from the conductivity measurement as a function of MWCNT loadings suggested two charge transport mechanisms: charge hopping in low MWCNT loadings (0.2-0.6 wt %) and ballistic conduction in high loadings (0.6-0.9 wt %). The composite exhibited dramatically enhanced conductivity up to 33 s·m$^{-1}$ at a low MWCNT loading (0.9 wt %). The results are discussed in more detail below.

Thermal gravimetric analysis ("TGA") was performed on the covalently linked MWCNT (0.33 wt %)-polystyrene composites, the MWCNT (0.33 wt %)-polystyrene blends, and the pristine polystyrene samples. The TGA experiments were performed under a nitrogen atmosphere to minimize the mass loss caused by nanotube oxidation, while allowing the polystyrene to thermally decompose completely. Comparison of the resulting thermograms between 0 and 700° C. revealed that the thermal degradation of all three samples proceeded by a one-step process with a maximum decomposition temperature. However, the temperature at the peak weight loss rate of the covalently linked MWCNT-polystyrene composite was approximately 15° C. higher than that observed for the MWCNT-polystyrene blend with the same composition, although an earlier onset of polymer decomposition for the covalently linked composite was observed as compared with the blend. The increase in thermal stability observed for the composite was attributed to an improved dispersion of the MWCNT's in the polymer matrix as well as the covalent bonding between the tube and the polymer.

Upon dissolution, the MWCNT-polystyrene composite formed a stable suspension in THF and remained well-dispersed after a one month period. Thin films of the nanocomposite were spin-cast from a THF solution. At lower MWCNT loadings (<0.9 wt %), a 500 μm thick film was optically transparent and no aggregation of the nanotubes was visually observed in the film. The HRTEM image of the composite showed that the MWCNT's were wrapped in the polymer matrix as bundles. Nanocomposite conductivity, as a function of dithioester MWCNT loadings, was measured on the spin-cast thin film by a two point probe method. Two point probe conductivity measurements were carried out on drop cast films of the nanocomposites, with different nanotube loadings, on vacuum deposited gold electrodes on glass. Contact across the electrode was made using gold wire and conductive Ag paint. Conductivity measurements were made using a Keithley 6487 Picoammeter/voltage supply. The plot of log$_{10}$ (conductivity) versus MWCNT wt % (0.02-0.9 wt %) suggested two distinct transport regions associated with nanotube loadings and corresponding polymerization (FIG. 9).

Figure 9:
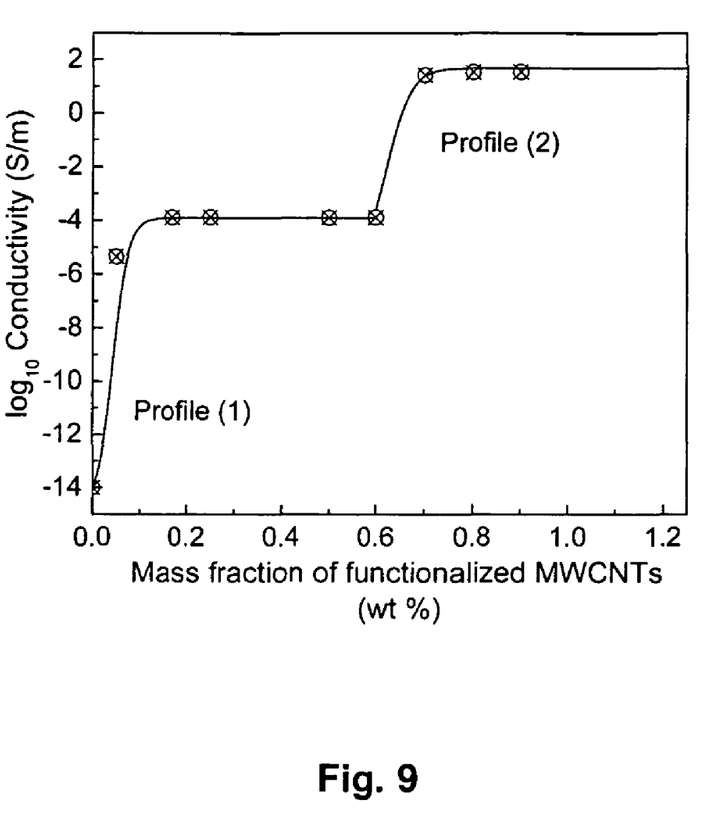
FIG. 9 shows a semi-logarithmic plot of covalently linked MWCNT-polystyrene composite conductivity as a function of mass fraction of MWCNT in polystyrene.

FIG. 9 shows a semi logarithmic plot of covalently linked MWCNT-polystyrene composite conductivity as a function of mass fraction of MWCNT in polystyrene. The solid line represents two curve fits using Eq. 1. For Profile (1) the parameters for best fit are: p<0.6 wt %; $p_{c1}$=0.0425 wt %; b=60; and for Profile (2) p≧0.6 wt %; $p_{c2}$=0.62 wt %; b=40.

Based on the Fermi-Dirac distribution, an analytical model (Eq. 1) has been proposed in the art to describe the critical insulator to conductor transition:

$$\log(\sigma_c) = \log(\sigma_n) + \frac{\log(\sigma_p) - \log(\sigma_n)}{1 + e^{[b(p-pc)]}} \qquad \text{Eq. 1}$$

Where $\sigma_c$, $\sigma_n$ and $\sigma_p$ are the conductivities of the composite, nanotubes, and pristine polymers respectively, p is the mass fraction of the nanotubes, and b is an empirical parameter that leads to the change in conductivity at the percolation threshold (or ballistic threshold) $p_c$. Eq. 1 was fitted to Profile (1) and (2) individually (FIG. 9). Profile (1) gives a percolation threshold ($p_{c1}$=0.0425 wt %) for lower MWCNT loadings, as a result of the homogeneity of the MWCNT's in the polystyrene matrix. This suggested a low microscopic phase transition between polymer and nanotubes that allowed charge transfer through a hopping transport regime. This resulted in an increase in conductivity from 10$^{-14}$ s·m$^{-1}$ for pure polystyrene to 10$^{-4}$ s·m$^{-1}$ at MWCNT loadings of 0.02-0.60 wt %. In profile (2), a second percolation threshold ($p_{c2}$=0.62 wt %) was seen with conductivities between 10$^{-4}$-33 s·m$^{-1}$ for nanotube loadings 0.60-0.90 wt %. In the art, a percolative description has been used to explain the connectivity of conductivity of a random two-phase system when examining nanotube-polymer composites.

In normal circumstances, the addition of nanotubes to an insulating matrix results in a singular percolative phenomena where the random distribution of the conductive matrix and hopping mechanism between the insulating barriers would determine the bulk conductivity of the system. The second regime that was observed was a result of the proximity of the nanotubes throughout the samples as a result of the formation of shorter polystyrene linkers at higher loadings of the chain transfer agent (dithiocarboxylic ester functionalized MWCNT's), rather than regions of isolated nanotube distribution that would normally conclude in hopping transport. Thus, the mechanism of charge hopping has now changed to fractional quantum conductance caused by nanotube proximity as a function of chemical modification and increased length scales of individual nanotubes.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all refer- ences, applications, patents, and publications cited above, and of the corresponding application(s), are hereby incorporated by reference.

What is claimed is:

1. A method of functionalizing at least one nanotube comprising:
   carboxylizing the at least one nanotube;
   reacting the at least one nanotube with a catalyst;
   activating at least one carboxylic functional group on the at least one nanotube for nucleophilic attack and;
   thiolating at least one hydroxyl and carbonyl functional group thereby thiolating the at least one nanotube.

2. The method of claim 1 wherein the catalyst comprises phosphorus pentasulfide.

3. The method of claim 1 wherein the carboxylizing step is performed in solution to prepare a dithiocarboxylic ester of the formula wherein MWCNT is a multi-walled carbon nanotube.

4. The method of claim 3 comprising reacting the at least one carbon nanotube and the catalyst in a solution comprising anhydrous toluene.

5. The method of claim 4 further comprising refluxing the solution.

6. The method of claim 5 comprising refluxing the solution for between approximately 10 and 50 hours at between approximately 0 and 150° C.

7. The method of claim 1 further comprising covalently bonding a first of the at least one nanotube to a second of the at least one nanotube and polymerizing the nanotubes.

8. The method of claim 7 wherein the covalently bonded nanotubes comprise nanotube dithioesters utilized as chain transfer agents for living free-radical polymerization of polymer monomers.

9. The method of claim 8 wherein the polymerization comprises Reversible Addition-Fragmentation Chain Transfer Polymerization.

10. The method of claim 9 further comprising:
    sonicating the nanotube dithioesters; and
    reacting the nanotube dithioesters with a polymer.

11. The method of claim 10 further comprising sonicating the nanotube dithioesters in a solution comprising anhydrous toluene.

12. The method of claim 10 wherein the polymer comprises styrene.

13. The method of claim 9 further comprising heating a reaction mixture comprising the nanotube dithioesters and the polymer.

14. The method of claim 13 further comprising:
    cooling the reaction mixture; and
    adding tetrahydrofuran to the reaction mixture.

15. The method of claim 13 further comprising adding the reaction mixture to methanol and precipitating a polymerized nanocomposite material.

16. The method of claim 1 wherein the catalyst comprises Lowesson's reagent.

* * * * *